United States Patent
Lorenz, II et al.

(10) Patent No.: US 9,145,345 B2
(45) Date of Patent: Sep. 29, 2015

(54) METHOD AND APPARATUS FOR PROCESSING GLYCOL

(71) Applicant: GlyEco, Inc., Phoenix, AZ (US)

(72) Inventors: John d'Arc Lorenz, II, Phoenix, AZ (US); Richard S. Geib, Madison, WI (US)

(73) Assignee: GlyEco, Inc., Phoenix, AZ (US)

( * ) Notice: Subject to any disclaimer, the term of this patent is extended or adjusted under 35 U.S.C. 154(b) by 72 days.

(21) Appl. No.: 13/843,105

(22) Filed: Mar. 15, 2013

(65) Prior Publication Data

US 2014/0066668 A1    Mar. 6, 2014

Related U.S. Application Data

(60) Provisional application No. 61/695,181, filed on Aug. 30, 2012.

(51) Int. Cl.
| | |
|---|---|
| *B01D 11/04* | (2006.01) |
| *B01D 17/12* | (2006.01) |
| *B01D 21/02* | (2006.01) |
| *B01D 21/24* | (2006.01) |
| *B01D 21/30* | (2006.01) |
| *B01D 36/00* | (2006.01) |

(Continued)

(52) U.S. Cl.
CPC .............. *C07C 29/76* (2013.01); *B01D 17/12* (2013.01); *B01D 21/02* (2013.01); *B01D 21/24* (2013.01); *B01D 21/30* (2013.01); *B01D 36/02* (2013.01); *B01D 36/04* (2013.01); *B01D 37/00* (2013.01); *C07C 29/88* (2013.01)

(58) Field of Classification Search
CPC .............. B01D 11/04; B01D 11/0488; B01D 11/0492; B01D 17/00; B01D 17/12; B01D 21/00; B01D 21/02; B01D 21/24; B01D 21/30; B01D 21/305; B01D 36/00; B01D 36/003; B01D 36/008; B01D 36/02; B01D 36/04; B01D 36/045; B01D 37/00; B01D 37/03; C07C 29/76; C07C 29/80; C07C 29/88; C07C 30/02; C08G 18/36; C11C 3/00
USPC ......... 202/176; 210/96.1, 202, 207, 209, 224, 210/231, 259, 335, 513, 534; 422/168, 162; 568/614, 617, 621, 852, 868, 913; 554/149, 174, 175

See application file for complete search history.

(56) References Cited

U.S. PATENT DOCUMENTS 2,793,235 A * 5/1957 Jenkinson ................ 568/871
3,252,897 A * 5/1966 Hesler et al. ............. 210/638

(Continued)

FOREIGN PATENT DOCUMENTS

| WO | 0206161 A2 | 1/2002 |
| WO | 2012109490 A2 | 8/2012 |

*Primary Examiner* — Joseph Drodge
(74) *Attorney, Agent, or Firm* — The Noblitt Group, PLLC

(57) ABSTRACT

Methods and apparatus for processing glycol according to various aspects of the present technology comprise a multi-stage treatment system that is configured to receive a feedstock from multiple waste stream sources containing glycol. A pre-treatment stage may be configured to process the incoming the feedstock and provide to a primary treatment stage a water/glycol solution that is substantially identical and allows for a primary treatment process that is not dependent upon the originating source of the glycol feedstock. A post-treatment stage may further process and purify the water/glycol solution.

9 Claims, 11 Drawing Sheets

(51) Int. Cl.
*B01D 37/00* (2006.01)
*C07C 29/76* (2006.01)
*C07C 29/80* (2006.01)
*C07C 29/88* (2006.01)
*B01D 36/04* (2006.01)
*B01D 36/02* (2006.01)

(56) References Cited

U.S. PATENT DOCUMENTS

| | | | | |
|---|---|---|---|---|
| 3,358,042 | A * | 12/1967 | Dunlop et al. | 568/617 |
| 3,441,616 | A * | 4/1969 | Pizzini et al. | 568/621 |
| 3,536,768 | A * | 10/1970 | Pitts | 568/871 |
| 3,809,724 | A * | 5/1974 | Golden | 568/858 |
| 3,816,485 | A * | 6/1974 | Wechsler | 554/134 |
| 4,113,662 | A * | 9/1978 | Wall | 502/329 |
| 4,371,713 | A * | 2/1983 | Matsumoto et al. | 568/614 |
| 4,879,049 | A | 11/1989 | De Mon et al. | |
| 5,021,152 | A | 6/1991 | Filowitz et al. | |
| 5,294,305 | A | 3/1994 | Craft et al. | |
| 7,157,607 | B1 * | 1/2007 | Sunkara et al. | 568/619 |
| 7,232,505 | B2 * | 6/2007 | Laborie et al. | 203/18 |
| 7,381,323 | B2 * | 6/2008 | Umezawa et al. | 210/108 |
| 8,114,957 | B2 * | 2/2012 | Niu et al. | 528/425 |
| 8,329,963 | B2 * | 12/2012 | Chen | 568/920 |
| 2004/0019235 | A1 * | 1/2004 | Martin et al. | 560/205 |
| 2004/0060870 | A1 | 4/2004 | Haddock et al. | |
| 2010/0041925 | A1 | 2/2010 | Reimann et al. | |
| 2010/0105966 | A1 | 4/2010 | Zhao et al. | |
| 2010/0133088 | A1 | 6/2010 | Hajek et al. | |
| 2011/0028371 | A1 * | 2/2011 | Rodrigues et al. | 510/220 |
| 2012/0323051 | A1 * | 12/2012 | Powell | 568/913 |

* cited by examiner

METHOD AND APPARATUS FOR PROCESSING GLYCOL

CROSS-REFERENCES TO RELATED APPLICATIONS

This application claims the benefit of U.S. Provisional Patent Application No. 61/695,181, filed Aug. 30, 2012, and incorporates the disclosure of the application by reference.

BACKGROUND

Automotive antifreeze consists of a base fluid of ethylene or propylene glycol and water into which are dissolved corrosion inhibitors, antifoaming additives, anti-scaling additives, dispersing agents and a distinctive dye. Virgin glycol-based antifreeze is usually made as a concentrated product (96% glycol and 4% additives and water) and it is used in engines at a lower concentration, diluted by water. Most antifreeze is used at a concentration of 40% to 60% glycol and 60% to 40% water. Making and shipping antifreeze as a concentrated product saves the freight cost of shipping water and reduces shipping costs per unit of concentrated antifreeze. In retail markets, more and more antifreeze is being packaged, shipped and sold as a 50% prediluted product, for consumer convenience.

Used antifreeze is usually contaminated with other used fluids from vehicle service work at a given facility. These fluids include used motor oil, used transmission fluid, used brake fluid, gasoline, and diesel fuel. Although separate disposal containers are usually provided, mechanics and service center employees don't always pay close attention as to which disposal container they are using for which used fluids. Used motor oil combined with lighter hydrocarbons, such as fuel, can form relatively stable emulsions with the water/glycol phase. The oil/hydrocarbon phase is usually less than 5% by volume, so an oil-in-water emulsion is formed.

Pretreatment of glycol-containing waste streams has involved gravity separation in storage without demulsifier assistance, wing-type oil/water separators, weir-type oil/water separators, flocculation/filtration, and simple filtration. All of these approaches are very labor intensive, produce widely varying results, and may leave behind a total hydrocarbon level of approximately 0.5%-1.0%. Residual hydrocarbons at these levels in the feed to the primary treatment may negatively impact the effectiveness of the primary treatment system.

SUMMARY

Methods and apparatus for processing glycol according to various aspects of the present technology comprise a multistage treatment system that is configured to receive a feedstock from multiple waste stream sources containing glycol. A pre-treatment stage may be configured to process the incoming feedstock and provide to a primary treatment stage a water/glycol solution that is substantially identical and allows for a primary treatment process that is not dependent upon the originating source of the glycol feedstock. A post-treatment stage may further process and purify the water/glycol solution.

BRIEF DESCRIPTION OF THE DRAWINGS

A more complete understanding of the present technology may be derived by referring to the detailed description when considered in connection with the following illustrative figures. In the following figures, like reference numbers refer to similar elements and steps throughout the figures.

DETAILED DESCRIPTION

The present technology may be described in terms of functional block components and various processing steps. Such functional blocks may be realized by any number of components configured to perform the specified functions and achieve the various results. For example, the present technology may employ various types of sensors, chemical treatment equipment, filtering systems, precipitation systems, fluid piping systems, storage equipment, and the like, which may carry out a variety of functions. In addition, the present technology may be practiced in conjunction with any number of processes such as distillation and/or filtration, and the system described is merely one example of an application for the present technology. Further, the present technology may employ any number of conventional techniques or control systems for dispersing chemicals, circulating air and fluids, detecting levels of chemical impurities, and/or sensing concentrations of particulates in fluids.

Methods and apparatus for processing glycol according to various aspects of the present technology may operate in conjunction with any suitable chemical treatment and/or recycling system. Various representative implementations of the present technology may be applied to any device capable of separating various phases of liquids, removing impurities, and/or identifying contaminants.

Figure 1:
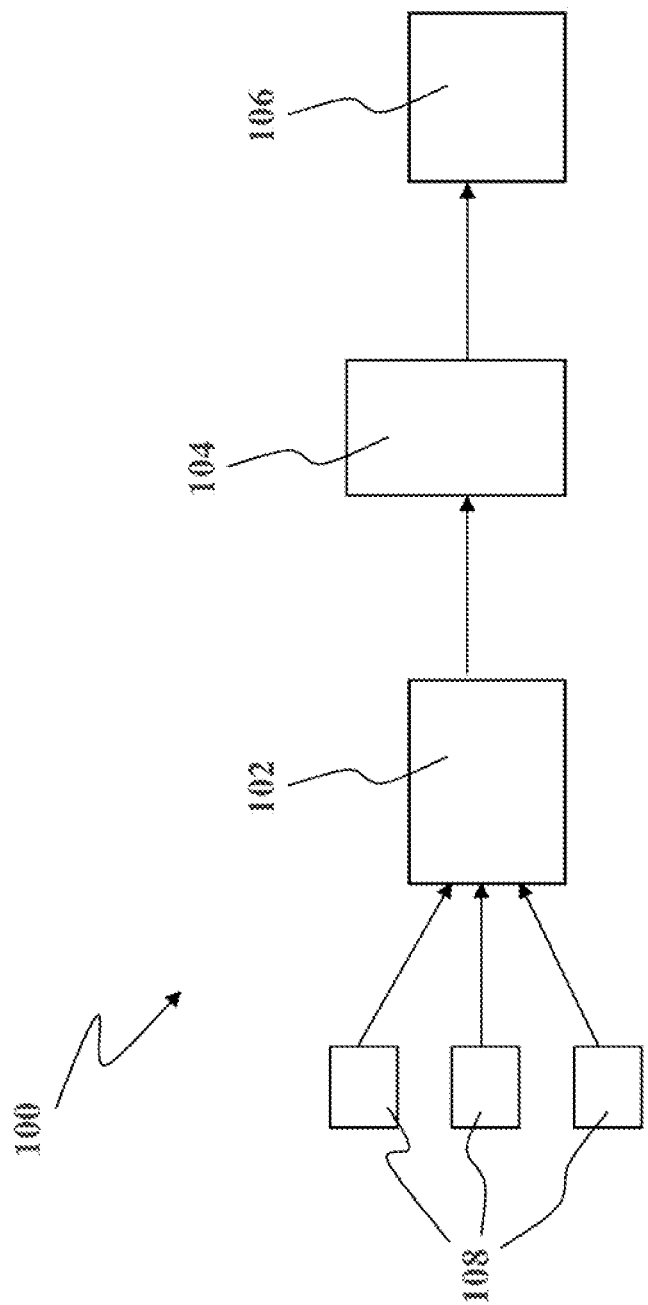
FIG. 1 representatively illustrates a multistage glycol treatment process in accordance with an embodiment of the present technology.

Referring now to FIG. 1, a glycol treatment system 100 for processing glycol according to various aspects of the present technology may comprise a material source 108 for providing glycol feedstock to the glycol treatment system 100. The glycol treatment system 100 may further comprise a pre-treatment system 102 for removing various impurities from the glycol feedstock, a primary treatment system 104 for removing additional impurities in the glycol feedstock and obtaining desired levels of recycled glycol, and a post-treatment process 106 for removing residual impurities.

The material source 108 for the glycol feedstock provides the glycol treatment system 100 with a supply of used glycol for treatment. The material source 108 may comprise any suitable form of compound or liquid containing glycol. For example, the material source 108 may comprise various manufacturing by-products or used compounds containing glycol such as ethylene carbonate manufacturing by-product waste streams, ethylene glycol manufacturing by-product waste streams, ethylene oxide sterilization process by-product waste streams, bio-mass and bio-fuel by-product waste streams, natural gas dehydration by-product waste streams, glycerin, used antifreeze, used aircraft deicing fluids, used heat exchange fluids, used inhibited glycol/water solutions, and the like. Each originating source of the glycol feedstock may comprise various impurities, contaminants, and/or other dissolved or suspended substances (e.g., particulates) in addition to glycol.

The pre-treatment system 102 processes the incoming material source 108 to provide a single supply of glycol feedstock to the primary treatment system 104. The pre-treatment system 102 may comprise any suitable device or method for receiving the incoming material source 108 and processing the glycol feedstock according to any suitable predetermined criteria. For example, the pre-treatment system 102 may treat the incoming material source 108 under one or more protocols determined according to any desired factors such as the originating source, the type of impurities present, and the level of a given impurity. In one embodiment, the pre-treatment system 102 may be suitably configured to sample the incoming material source 108 to determine a type or level of impurity present and direct the incoming material source 108 to the appropriate protocol.

Figure 2:
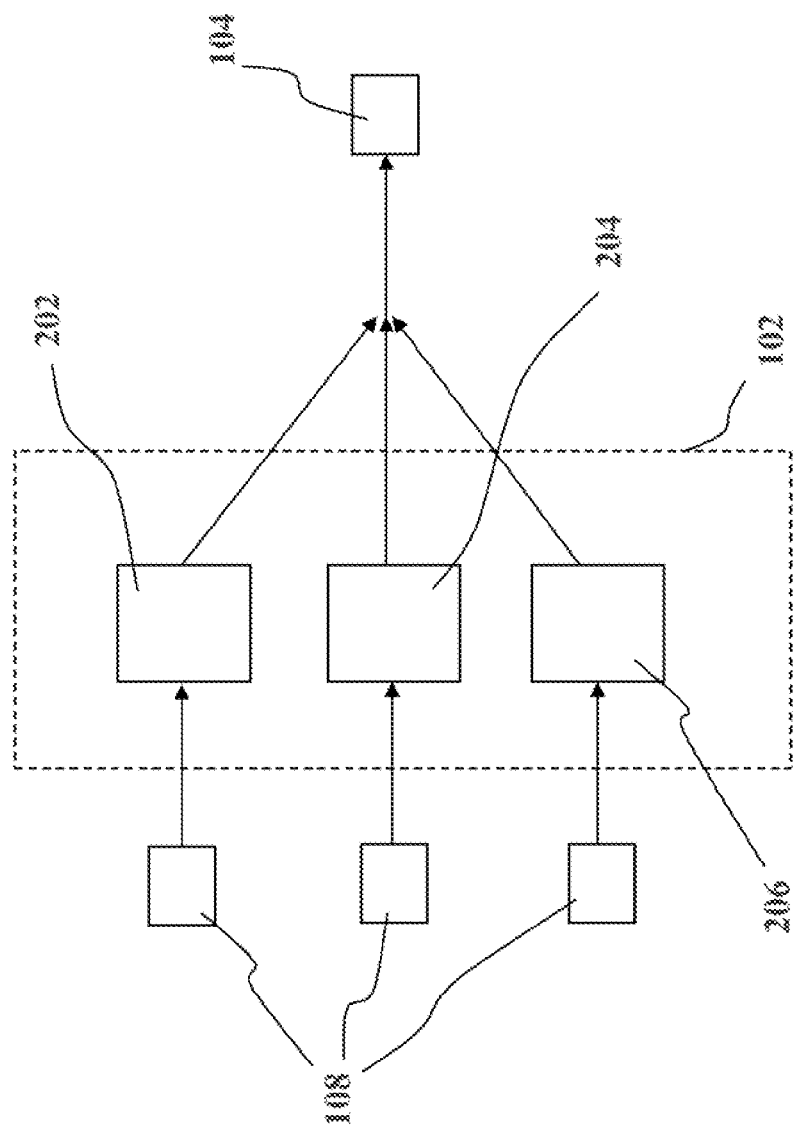
FIG. 2 representatively illustrates a pre-treatment system in accordance with an embodiment of the present technology.

The pre-treatment system 102 may comprise one or more devices, system, or processing lines to process the incoming material source 108. For example, referring now to FIG. 2, the pre-treatment system 102 may comprise multiple processing lines directed towards identifying and treating different waste streams containing glycol. In one embodiment, the pre-treatment system 102 may comprise a system to treat used heat exchange fluid 202, a treatment system for by-products of polyester fiber manufacturing 204, and a treatment system for by-products resulting from ethylene-oxide sterilization 206. Each processing line may process the incoming material source 108 in such a manner that the resulting glycol feedstock provided to the primary treatment system 104 allows for a primary treatment process that is not dependent upon the originating source of the glycol feedstock.

Figure 3:
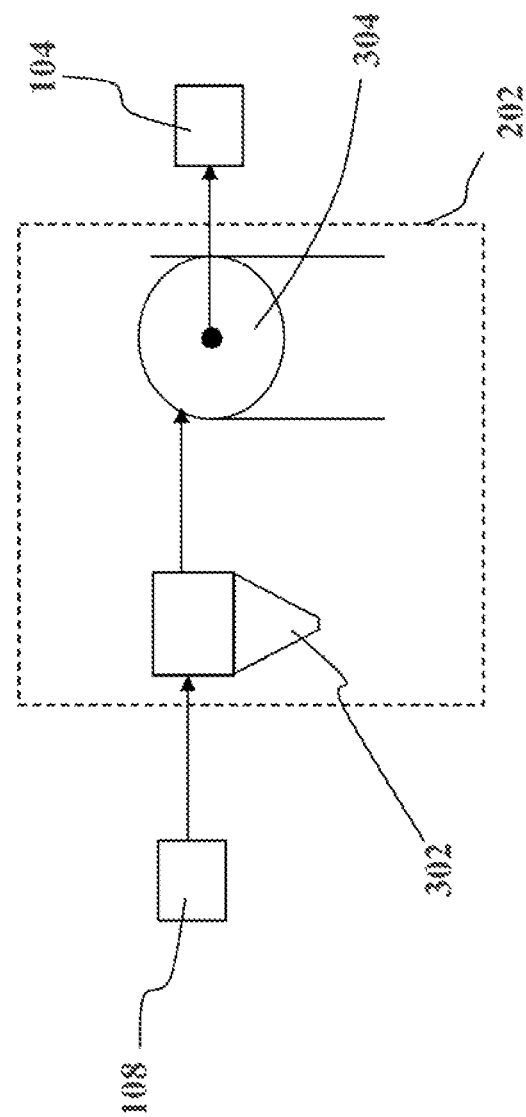
FIG. 3 representatively illustrates a hydrocarbon separation system in accordance with an embodiment of the present technology.

The heat exchange fluid feedstock treatment system 202 removes hydrocarbon based impurities from the incoming material source 108. The heat exchange fluid feedstock treatment system 202 may be suitably adapted to process recycled glycol sources such as used antifreeze, used aircraft deicing fluids, and used heat exchange fluids. Each of these sources may comprise various levels of hydrocarbon impurities that may impact the ability to successfully separate the impurities from the glycol. Referring now to FIG. 3, the heat exchange fluid feedstock treatment system 202 may comprise a hydrocarbon separation system 302 for separating hydrocarbons from the glycol feedstock and a filtration system 304 for collecting residual hydrocarbon impurities.

The hydrocarbon separation system 302 may comprise any suitable method for separating impurities such as gravity separation, a floating wing separator, media filtration, molecular sieve, hydrocyclone, centrifuge, and the like. For example, in one embodiment, the hydrocarbon separation system 302 may inject a demulsifying agent into the incoming material source 108 to facilitate the separation of the hydrocarbon phase from the water/glycol phase. The demulsifying agent may comprise any suitable chemical or compound such as: cationic polyacrylamide based compounds, polymer and alcohol compounds, epoxy resins, polyamines, di-epoxides, melamine resins, melamine-formaldehyde polymers, phenol-formaldehyde resins, and the like. For example, in one embodiment, the demulsifying agent may comprise a compound having a molecular weight of 4,000-6,000 and be adapted to separate the hydrocarbon phase from the water/glycol phase at ambient temperatures of between about 30° to 100° Fahrenheit and be configured to provide separation of the hydrocarbon phase in a matter of hours resulting in an approximate separation level of about 99.90% to 99.95% hydrocarbon phase from the water/glycol phase. In another embodiment, the demulsifying agent may comprise a polymer and alcohol compound adapted for use at temperatures of between about 40° to 100° Fahrenheit and be configured to provide separation of the hydrocarbon phase resulting in an approximate separation, level of at least about 95% of the hydrocarbon phase from the water/glycol phase.

Separation of the phases may be achieved through gravity separation alone or additional methods may be used to improve separation efficiency. For example, flocculation and/or temperature control of the combined demulsifying agent and the incoming material source 108 may be utilized to help increase the rate at which the hydrocarbons are separated from the water/glycol phase.

The filtration system 304 receives the water/glycol phase of the separated glycol feedstock from the hydrocarbon separation system 302 and further processes the water/glycol phase to remove residual hydrocarbons not collected by the hydrocarbon separation system 302. The filtration system 304 may comprise any suitable device or system for removing impurities from the glycol feedstock. For example, the filtration system 304 may comprise a filter utilizing a filter medium suitably adapted to absorb hydrocarbons from the water/glycol phase as the glycol feedstock is passed through the filter. In one embodiment, the filtration system 304 may comprise a rotary vacuum filter drum having a filter aid adapted to absorb hydrocarbons of various weights. The filter aid may comprise any suitable material such as diatomaceous earth, perlite, activated carbon, bentonite clay, or any combination of one or more elements.

For example, the filter aid may comprise a first absorbing element configured to absorb heavier hydrocarbons such as motor oil, dissolved greases, and tar-like degradations and a second absorbing element configured to absorb lighter hydrocarbons such as fuels and washer solvents. The filter aid may further comprise an element configured to maintain predetermined flow rate of the glycol feedstock through the filter as the hydrocarbons are separated from the water/glycol phase. The elements may be combined in any suitable order, volume, or weight according to any predetermined criteria. For example, in one embodiment, the filter aid may comprise a combination of up to about 30% by weight of activated carbon, up to about 30% by weight of bentonite clay, and 40%-60% by weight of diatomaceous earth.

The treatment system for by-products of polyester fiber manufacturing 204 may process the incoming source material 108 to remove impurities from the glycol feedstock formed as a by-product of the esterification of dicarboxylic acids and dihydroxy alcohols (glycols). For example, Polyester fiber is commonly made by reacting a glycol with terephthalic acid. The glycol most commonly used in the manufacture of polyester fibers and resins is ethylene glycol. It may be the only glycol used, or it may be used in combination with other glycols, including diethylene glycol, triethylene glycol, and propylene glycol. Similarly, polyester resins are made with a broader range of dicarboxylic acids such as maleic, fumaric, phthalic and adipic acids. One or more different glycols may be reacted with the dicarboxylic acids to produce fiber or resin with certain properties.

When a polyester producer changes the type of polyester that he is making, the glycol(s), which serves as the carrier fluid for the reaction, is purged from the system, and the production of a new type of polyester is begun. Polyester fiber/resin manufacturing plants often include processing steps to minimize the quantity of longer chain polymers/esters that are lost in the purged glycols. Therefore, it may be likely that if the incoming material source 108 is from the polyester fiber/resin manufacturing plant, the only esters present in the purged glycols are shorter chain esters, such as ethyl acetate, ethylene glycol monoacetate, and diethyl acetate.

Figure 4:
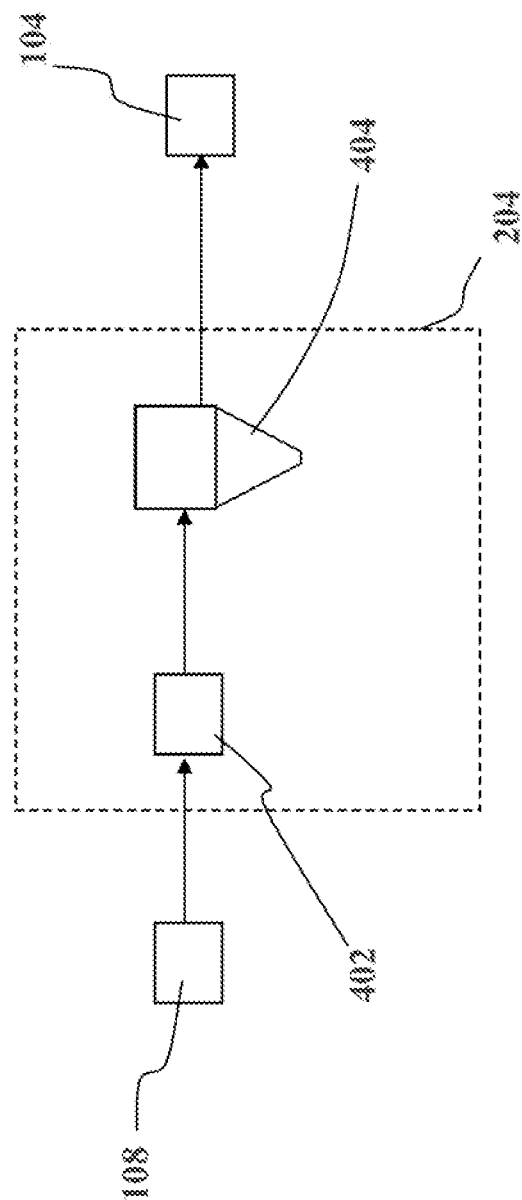
FIG. 4 representatively illustrates a polyester fiber treatment system in accordance with an embodiment of the present technology.

Referring now to FIG. 4, the treatment system for by-products of polyester fiber manufacturing 204 may comprise a filter system 402 for removing oligomers and an ester treatment system 404 for hydrolyzing esters. The filter system 402 may comprise any suitable device or system for filtering molecules having a limited number of monomers such as paraffins, plasticizers, and the like. For example, the filter system 402 may comprise a filter press, a hydrocyclone, or similar mechanical filter.

The ester treatment system 404 processes the glycol feedstock to hydrolyze esters that may be present in the incoming material source 108. The ester treatment system 404 may comprise any suitable system or device for hydrolyzing esters to form organic acids and alcohols. For example, the ester treatment system 504 may comprise a saponification-like process to cleave esters from the glycol feedstock into their component acids and alcohols by injecting an alkali into the glycol feedstock. In one embodiment, the ester treatment system 404 may inject an amount of a low chloride sodium hydroxide aqueous solution into the glycol feedstock to hydrolyze any present esters.

The amount of alkali injected into the glycol feedstock may be determined by measuring an ester level in the water/glycol feedstock. The ester level may be measured by any suitable method or process such as by a back titration method. Based on the measured level of esters present, the ester treatment system 404 may be suitably configured to add an amount of alkali to completely hydrolyze the esters. Alternatively, the amount of alkali injected into the glycol feedstock may be greater than that needed to completely hydrolyze the esters. For example, a predetermined excess amount of alkali may be used such that at least a portion of any organic acids created as a result of the hydrolyzed esters are neutralized by the excess alkali. The neutralized acids may fob a sodium salt that may be treated in a later stage according to its water solubility.

The alkali may comprise any suitable base compound such as sodium hydroxide, potassium hydroxide, barium hydroxide, cesium hydroxide, calcium hydroxide and the like. Additionally, weak acids such as formic acid, hydrofluoric, acetic, hydrogen peroxide, and the like may be used depending upon any predetermined criteria such as the type or level of esters present or the desired type of organic acid and alcohol by-product.

The treatment system for by-products resulting from ethylene-oxide sterilization 206 may process the incoming source material 108 to remove impurities from the glycol feedstock formed as a by-product of the use of ethylene oxide. For example, ethylene oxide gas is used to sterilize medical and analytical instruments. The ethylene oxide gas is introduced into a chamber which holds the equipment to be sterilized, is allowed to contact the equipment, and is then thoroughly removed from the chamber by a vacuum pump. A packed contacting column is located between the chamber and the vacuum pump. The used ethylene oxide gas is pulled upward through this column while concentrated sulfuric acid flows downward through the packing. The sulfuric acid catalyzes the conversion of the ethylene oxide gas to ethylene glycol. This reaction also produces some amount of esters and ester acids, and small quantities of higher glycols, including diethylene and triethylene glycols. The excess acid that remains with the ethylene glycol is then neutralized with a sodium hydroxide/water aqueous solution. This neutralization reaction produces sodium sulfate. Thus, the by-product ethylene glycol is contaminated with sodium sulfate, water, esters, and small percentages of higher glycols. The concentration of ethylene glycol in this by-product stream may have a range of 40% to 60% and contain sodium sulfate at a rate of between about 2,000-20,000 parts per million.

Figure 5:
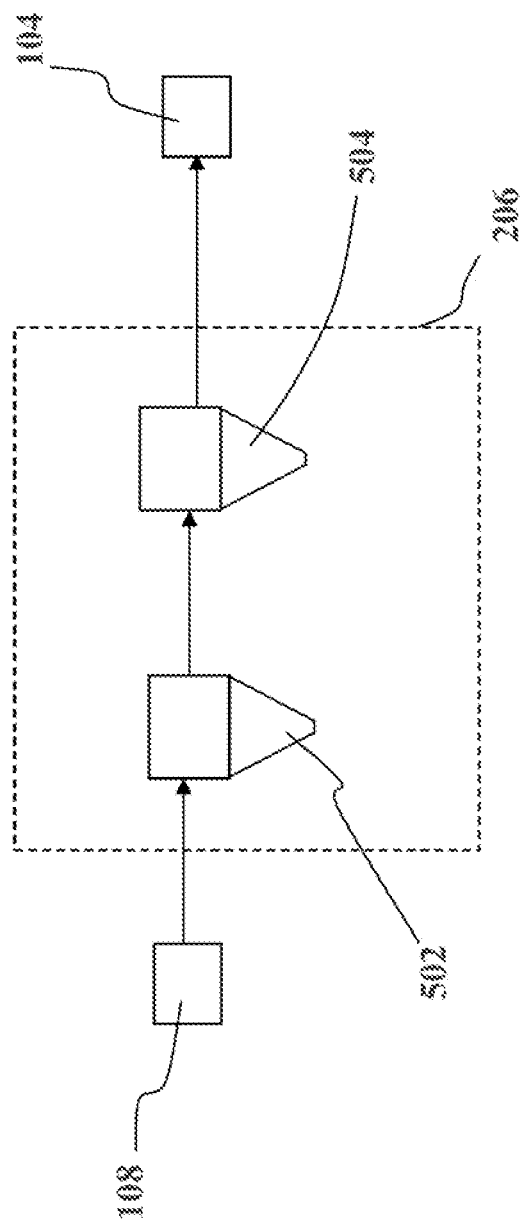
FIG. 5 representatively illustrates an ethylene sterilization treatment system in accordance with an embodiment of the present technology.

The treatment system for by-products resulting from ethylene-oxide sterilization 206 may be adapted to process ethylene glycol by any suitable device or method. Referring now to FIG. 5, the treatment system for by-products resulting from ethylene-oxide sterilization 206 may comprise a sulfate precipitation system 502 for precipitating sulfates out of the glycol feedstock and an ester treatment system 504 for hydrolyzing esters.

The sulfate precipitation system 502 removes sodium sulfate impurities from the incoming material source 108. The sulfate precipitation system 502 may comprise any system or device for reducing a level of sulfates present in a solution. In one embodiment, the sulfate precipitation system 502 may comprise a cone bottom tank configured to inject a sulfate precipitator into the incoming supply of glycol feedstock. The sulfate precipitator may comprise any suitable chemical or solution adapted to convert at least a portion of liquid phase sulfates into a heavy solid that settles to a lower portion of the cone bottom tank where the sulfates may then be separated from the remaining water/glycol phase. For example, sulfate precipitator may comprise an alkali adapted to precipitate the sodium sulfate to make a solid sulfate compound and sodium hydroxide. The sulfate precipitation system 502 may use any suitable alkali such as sodium hydroxide, potassium hydroxide, calcium hydroxide, magnesium hydroxide, and barium hydroxide. The sulfate compound may settle out leaving the sodium hydroxide in suspension resulting in a residual alkalinity level to the water/glycol solution. The residual alkalinity level may help maintain the water/glycol solution in a desired pH range during additional process steps and prevent glycol from degrading into glycolic acids.

The ester treatment system 504 processes the glycol feedstock to hydrolyze esters that may be present in the incoming material source 108. The ester treatment system 504 may comprise any suitable system or device for hydrolyzing esters to form organic acids and alcohols. For example, the ester treatment system 504 may comprise a saponification-like process to cleave esters from the glycol feedstock into their component acids and alcohols by injecting an alkali into the glycol feedstock. In one embodiment, the ester treatment system 504 may inject an amount of a low chloride sodium hydroxide aqueous solution into the glycol feedstock to hydrolyze any present esters.

The amount of alkali injected into the glycol feedstock may be determined by measuring an ester level in the water/glycol feedstock. The ester level may be measured by any suitable method or process such as by a back titration method. Based on the measured level of esters present, the ester treatment system 504 may be suitably configured to add an amount of alkali to completely hydrolyze the esters. Alternatively, the amount of alkali injected into the glycol feedstock may be greater than that needed to completely hydrolyze the esters. For example, a predetermined excess amount of alkali may be used such that at least a portion of any organic acids created as a result of the hydrolyzed esters are neutralized by the excess alkali. The neutralized acids may form a sodium salt that may be treated in a later stage according to its water solubility.

The alkali may comprise any suitable base compound such as sodium hydroxide, potassium hydroxide, barium hydroxide, cesium hydroxide, calcium hydroxide and the like. Additionally, weak acids such as formic acid, hydrofluoric, acetic, hydrogen peroxide, and the like may be used depending upon any predetermined criteria such as the type or level of esters present or the desired type of organic acid and alcohol by-product.

The ester treatment system 504 may comprise a standalone process or it may be integrated into the sulfate precipitation system 502. For example, in one embodiment, the ester treatment system 504 may comprise a cone bottom tank configured to receive the glycol feedstock from the sulfate precipitation system 502. In another embodiment, the ester treatment system 504 may be integrated into the same tank system as that used in the sulfate precipitation system 502.

Figure 6:
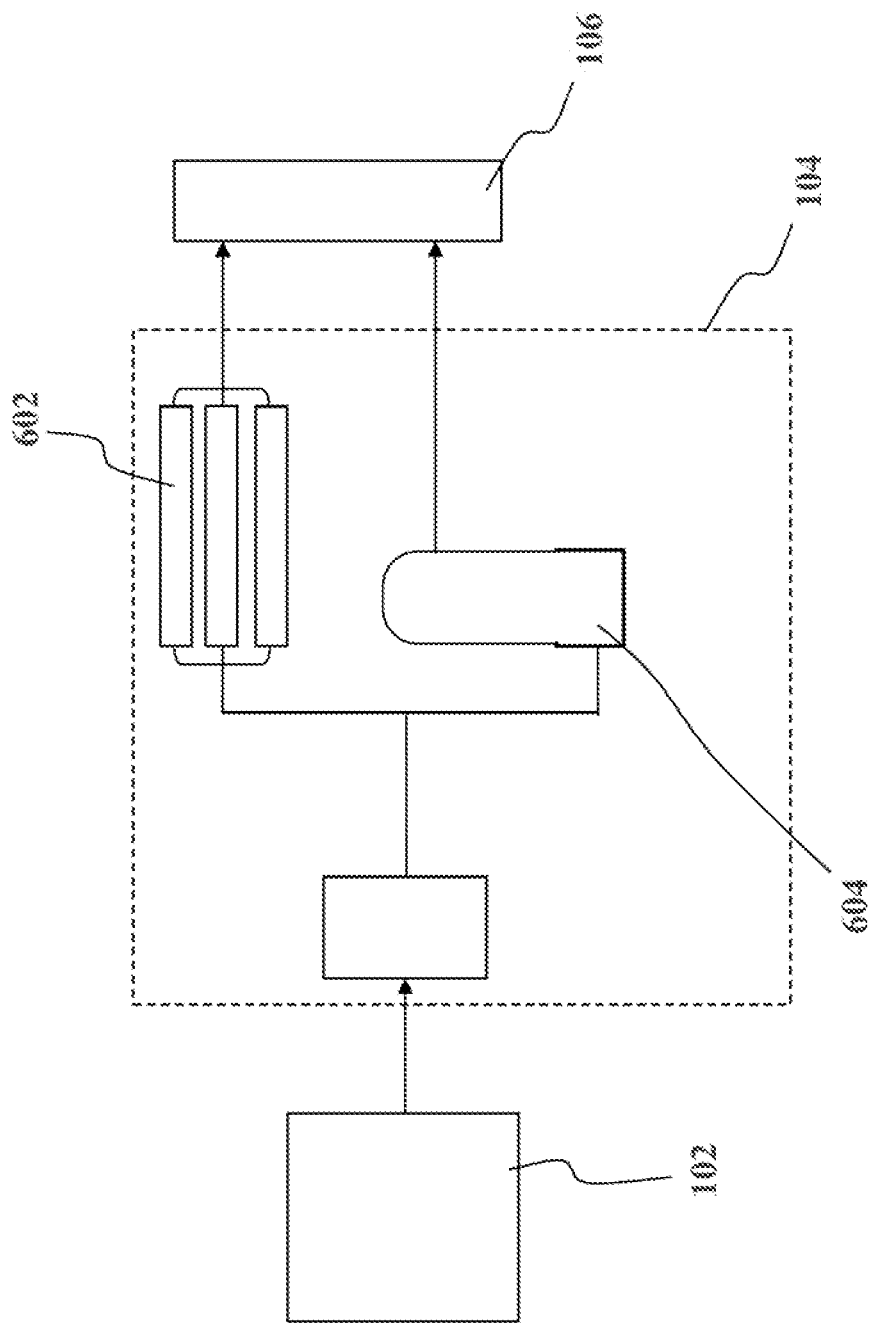
FIG. 6 representatively illustrates a primary treatment system in accordance with an embodiment of the present technology.

The primary treatment system 104 receives the glycol feedstock from the pre-treatment system 102 and removes dissolved solids and other impurities from the pretreated feedstock. The primary treatment system 104 may comprise any suitable system or method for processing the pre-treated glycol feedstock. Referring now to FIG. 6, the primary treatment system 104 may comprise multiple processing lines configured to operate in parallel, wherein in processing line is directed towards producing a desired concentration ratio of ethylene glycol to water. For example, the primary treatment system 104 may comprise a filtration system 602 for producing a concentration of ethylene glycol to water less than about 50% and a distillation system 604 for producing a concentration of ethylene glycol to water that is in excess of about 97%. The resulting ethylene glycol to water solution of the primary treatment system may be directed to the post-treatment system 106 for additional processing. In an alternative embodiment, the primary treatment system 104 may comprise a single processing line dedicated to producing a desired concentration level of ethylene glycol to water.

The filtration system 602 may comprise any system or device or removing dissolved impurities from the glycol feedstock. For example, in one embodiment, the filtration system 602 may comprise a nano filtration system adapted to collect organic molecules with a molecular weight greater than about 200. Ethylene glycol has a molecular weight of 62.1 and water has a molecular weight of 18. Accordingly, each is able to pass through the nano filtration system. The nano filtration system may also be configured to collect strongly charged divalent and higher ions.

Figure 7:
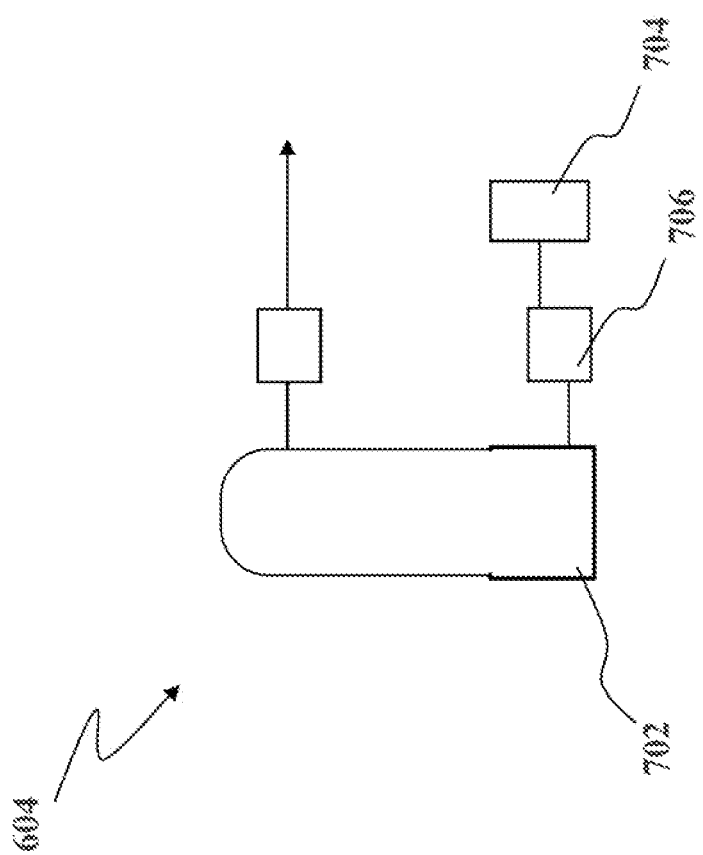
FIG. 7 representatively illustrates a distillation tower in accordance with an embodiment of the present technology.

The distillation system 604 processes the glycol feedstock to separate impurities according to a volatility of individual components within the glycol feedstock. The distillation system 604 may comprise any system to method for separating ethylene glycol from water and other dissolved solids. For example, in one embodiment, the distillation system 604 may comprise a vacuum distillation tower 606 suitably configured to product concentrated ethylene glycol by separating undesired impurities according to their boiling points. Referring again to FIG. 7, the distillation tower 606 may comprise a vacuum distillation column 702 having a predetermined number of trays according to a desired concentration level. The distillation tower 606 may also comprise a reboiler 704 for heating the glycol feedstock, and a vacuum pump 706 for producing a vacuum pressure.

The distillation system 604 may produce a high concentration ethylene glycol at a relatively low temperature. The vacuum pump 706 may comprise any suitable pump configured to achieve a desired level of vacuum. For example, in one embodiment, the vacuum pump 706 may be adapted to provide a vacuum of about 26 inches of mercury (Hg), or a pressure of about 100 mm Hg to allow distillation to be performed at a temperature of about 260° Fahrenheit or less. Distilling glycol at this temperature may reduce glycol degradation and may also reduce the heat input requirement required. The heat input requirement may be further reduced by preheating the feed to the vacuum distillation column 702 with ethylene glycol from the product condenser. For example, condensed glycol may be about 150° Fahrenheit, and may be pumped through a shell side of a heat exchanger. This may result in elevating a temperature of the feed to the vacuum distillation column 702 to 135°-140° Fahrenheit, while reducing the temperature of the distilled ethylene glycol to approximately the same level.

The primary treatment system 104 may be configured to improve the overall yield by reducing an amount of water/glycol solution that might be lost through one or more system processes. For example, in one embodiment, the filtration system 602 may produce a by-product volume of approximately 35% ethylene glycol to water. This by-product volume may be routed to an input of the distillation system 604 where it is combined with the glycol feedstock coming from the pre-treatment system 102 where as much as 95% of the glycol by-product from the filtration system 602 may be recovered.

Figure 8:
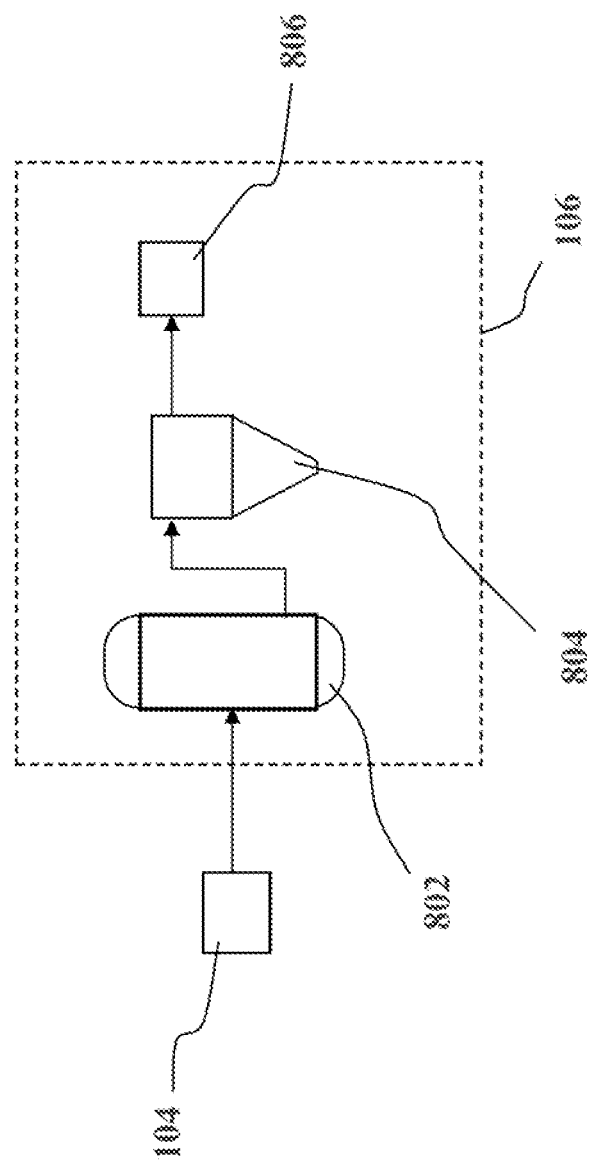
FIG. 8 representatively illustrates a post-treatment system in accordance with an embodiment of the present technology.

The post-treatment system 106 processes a concentrated level of glycol/water to remove residual impurities not captured by the pre-treatment system 102 and the primary treatment system 104. The post-treatment system 106 may comprise any suitable system or method for collecting or treating impurities. For example, referring to FIG. 8, the post-treatment system 106 may comprise a deionization system 802, a compound oxidation system 804, and a polishing system 806. The post-treatment system 106 may be configured to remove any remaining impurities such that the resulting recycled glycol/water solution meets ASTM E1177 Type I specifications for pure glycol.

Figure 9:
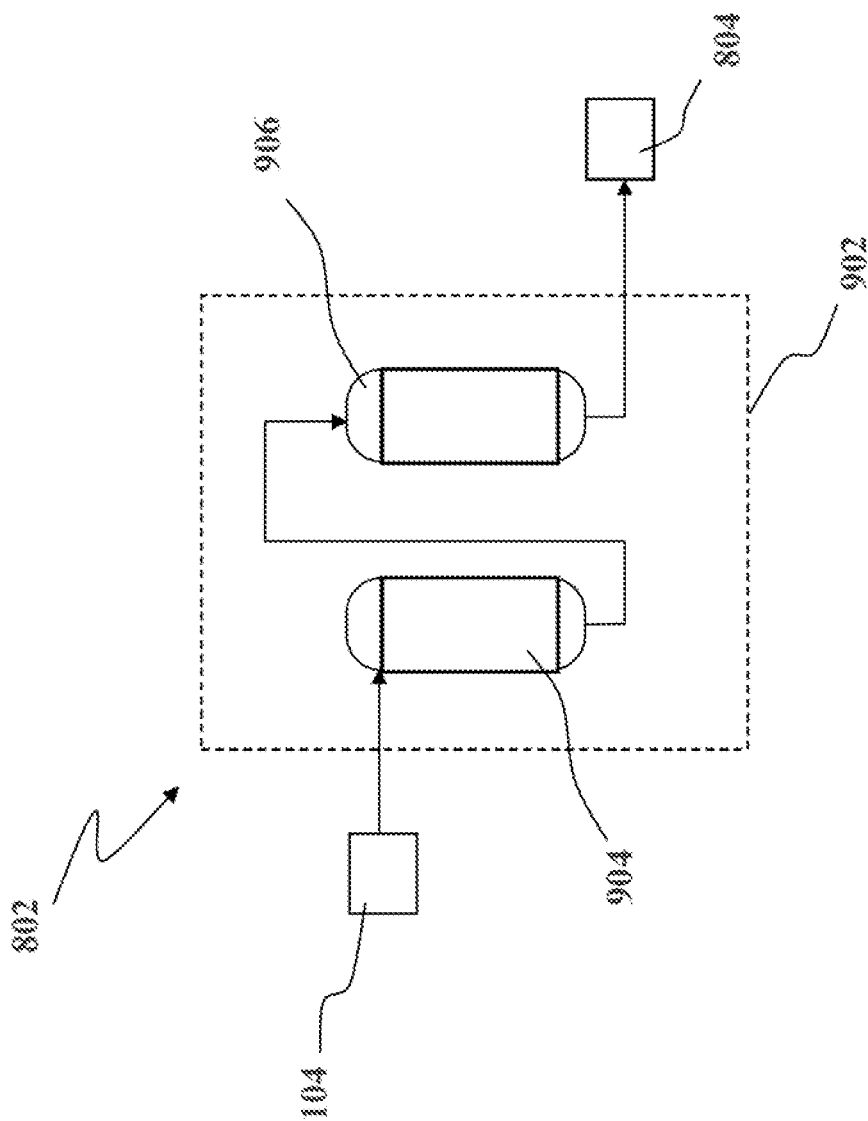
FIG. 9 representatively illustrates a deionization system in accordance with an embodiment of the present technology.

The deionization system 802 may comprise any suitable device or system for removing ions from the glycol/water solution. For example, the deionization system 802 may be suitably adapted to remove iconic species such as monovalent ions not separated during any other processing stage. Referring now to FIG. 9, in one embodiment, the deionization system 802 may comprise a dual bed ion exchange unit 902 having an anion exchange bed 904 and a cation exchange bed 906. In another embodiment, the deionization system 802 may comprise an ion exchange unit having only a single strong anion exchange resin bed. For example, the anion exchange resin bed may comprise a "type 2" strong base anion resin incorporating a styrene-divinylbenzene copolymer reacted with dimethylethanolamine.

Figure 10:
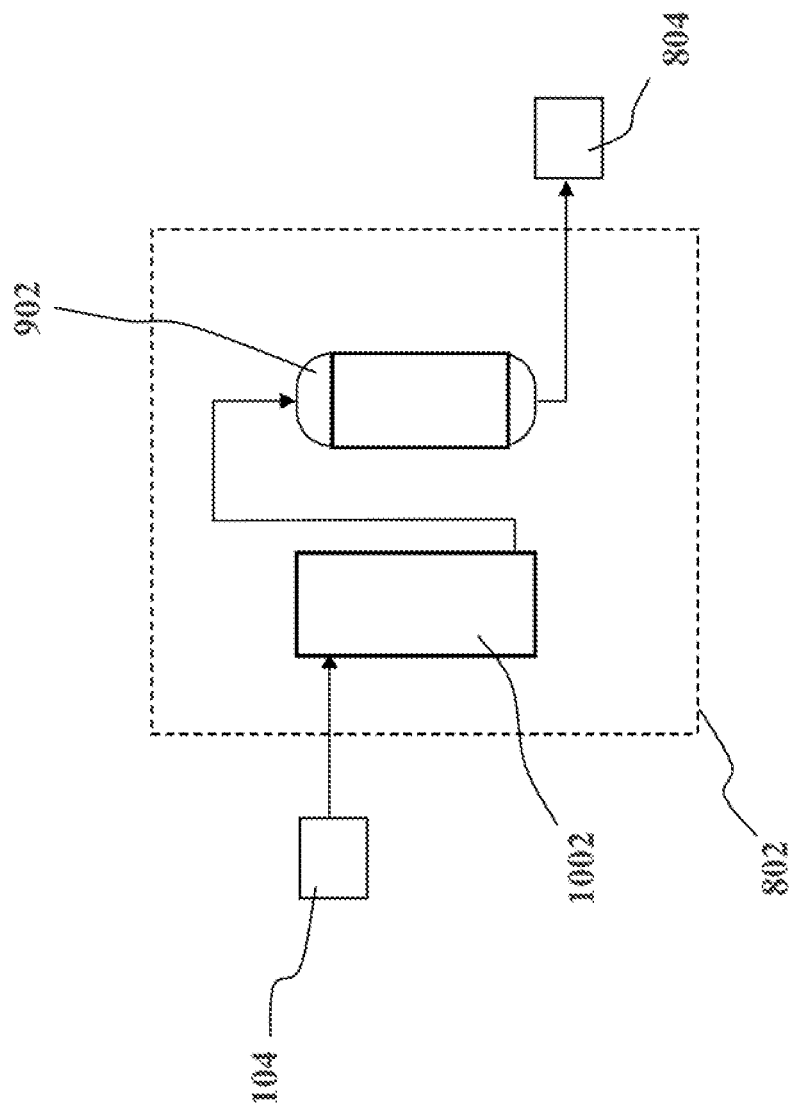
FIG. 10 representatively illustrates a deionization system and an electrodialysis unit in accordance with an embodiment of the present technology.

Referring now to FIG. 10, in another embodiment, the deionization system 802 may comprise an electrodialysis unit 1002 positioned in line with a dual bed ion exchange unit 1004. The electrodialysis unit 1002 may comprise any suitable system for transferring ions between two or more solutions under the influence of an electric potential difference. For example, the electrodialysis unit 1002 may be configured with 12 cell pairs, with an applied voltage of 2.5 volts per cell.

In one embodiment, the cell pairs may comprise any suitable combination of homogeneous, strong acid and homogeneous strong base ion exchange membranes according to a desired level of ion removal.

Figure 11:
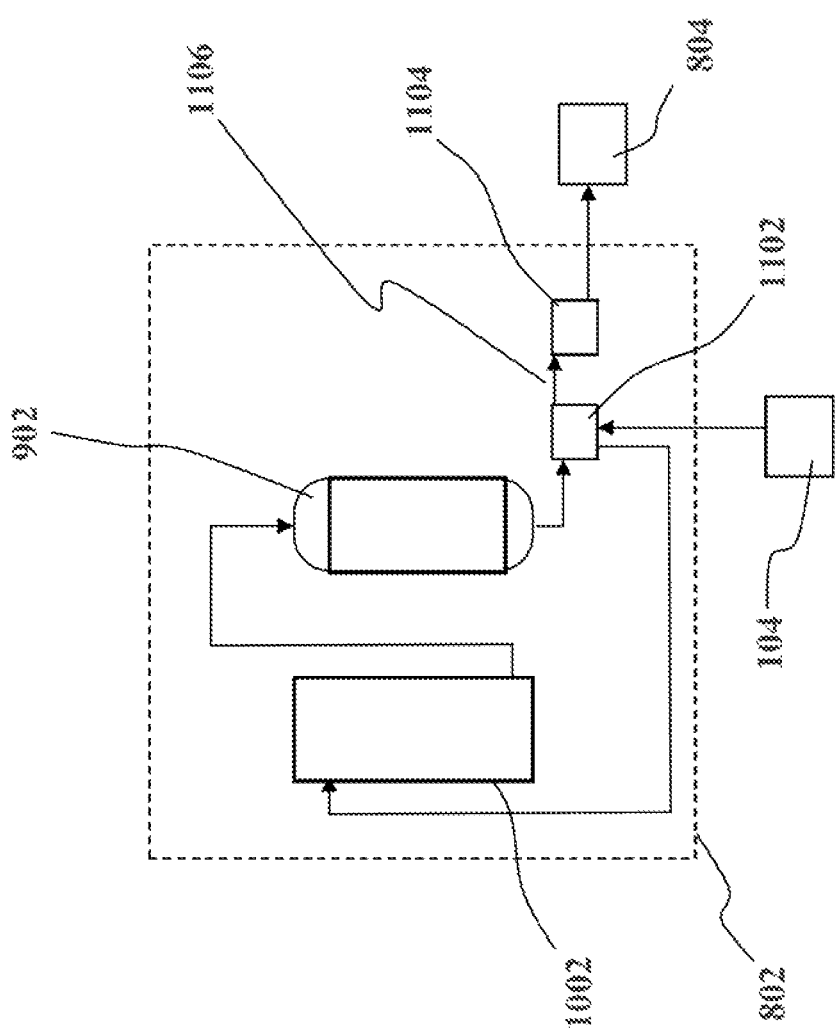
FIG. 11 representatively illustrates a deionization system and a surge tank unit in accordance with an embodiment of the present technology.

Referring now to FIG. 11, the deionization system 802 may further comprise a surge tank 1102 for recirculating the glycol/water solution through the ion exchange unit and/or electrodialysis unit to increase an ion removal rate through the ion exchange unit and an overflow tank 1104 for receiving an overflow of deionized glycol solution from the surge tank 1102. The surge tank 1102 may comprise any suitable device or system for recirculating the glycol/water solution through the deionization system 802. The overflow tank 1104 may comprise and suitable device for receiving deionized the glycol/water solution from the surge tank 1102. For example, in one embodiment, the overflow tank 1104 may be connected to the surge tank 1102 by a fluid line 1106 positioned along a top surface of the glycol/water solution in the surge tank 1102.

The compound oxidation system 804 removes color and odor causing compounds from the glycol/water solution. The compound oxidation system 804 may comprise any suitable system or method for oxidizing double bonds, or alternating double and single bonds in organic compounds such as compounds left over from corrosion inhibitors in used antifreeze, impurities introduced into used antifreeze via engine combustion blow-by gasses, and/or from impure water dilution. For example, in one embodiment, the compound oxidation system 804 may comprise a tank separator configured to inject an alkali into the water/glycol solution to increase a pH level of the water/glycol solution to approximately 11.0-11.5. The alkali used may be added in any suitable amount to produce the desired pH level. For example, in one embodiment the alkali may comprise a 45% solution of potassium hydroxide added in sufficient volume to produce the desired pH level. In another embodiment, the alkali may comprise an aqueous solution of sodium hydroxide added in sufficient volume to produce the desired pH level.

The compound oxidation system 804 may be further configured to inject an oxidizer such as hydrogen peroxide to form perhydroxyl (OOH—) free radicals. The oxidizer may be added in any suitable volume or concentration level. For example, a 50% hydrogen peroxide solution may be added to the tank separator at a level of between 0.1%-3.0% by volume. The tank separator may be further configured to agitate the water/glycol and oxidizer to facilitate decomposition of organic compounds by the oxidizer.

The compound oxidation system 804 may further comprise a measuring system configured to monitor the level of the oxidizer during the reaction process. For example, the measuring system may be adapted to signal the compound oxidation system 804 to continue the reaction process until a desired level of residual oxidizer is left in the water/glycol solution. In one embodiment, the measuring system may be configured to continue the reaction process until a chlorine electrode indicates that the residual level of oxidizer has reached a threshold level of less than about 20 parts per million. In another embodiment, the threshold level may be less than about 10 parts per million.

Individual processes in the post-treatment system 106 may be arranged in any order according to a desired outcome. Similarly, individual processes in the post-treatment system 106 may be incorporated into the pre-treatment system 102 and/or the primary treatment system 104.

The particular implementations shown and described are illustrative of the present technology and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent examples of functional relationships and/or steps between the various elements. Many alternative or additional functional relationships or physical connections may be present in a practical system.

In the foregoing specification, the present technology has been described with reference to specific embodiments. Various modifications and changes may be made, however, without departing from the scope of the present technology as set forth in the claims. The specification and figures are illustrative, rather than restrictive, and modifications are intended to be included within the scope of the present technology. Accordingly, the scope of the present technology should be determined by the claims and their legal equivalents rather than by merely the examples described.

For example, the steps recited in any method or process claims may be executed in any order and are not limited to the specific order presented in the claims. Additionally, the components and/or elements recited in any apparatus claims may be assembled or otherwise operationally configured in a variety of permutations and are accordingly not limited to the specific configuration recited in the claims.

Benefits, other advantages and solutions to problems have been described above with regard to particular embodiments; however, any benefit, advantage, solution to problem or any element that may cause any particular benefit, advantage or solution to occur or to become more pronounced are not to be construed as critical, required or essential features or components of any or all the claims.

As used herein, the terms "comprise", "comprises", "comprising", "having", "including", "includes" or any variation thereof are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The invention claimed is:

1. A system for removing impurities from an incoming waste stream of glycol feedstock, comprising:
   an ester treatment device configured to:
      receive the incoming waste stream of glycol feedstock;
      determine an ester level within the incoming waste stream of glycol feedstock;
      inject a stoichiometric excess of alkali solution into the incoming waste stream of glycol feedstock comprising residual alkali solution and a pH of greater than 7, wherein the stoichiometric excess is:
         calculated according to the determined ester level; and
         sufficient to completely hydrolyze the esters to yield constituent insoluble organic acid salts and organic alcohols; and
      precipitate the insoluble organic acid salts from the incoming waste stream of glycol feedstock.

2. A system for removing impurities from an incoming waste stream of glycol feedstock according to claim 1, wherein the ester treatment device comprises:
a cone bottom tank having a fluid line; and
a filter disposed within the fluid line, wherein the filter is configured to:
contact the incoming waste stream of glycol feedstock as the feed flows through the fluid line; and
separate the insoluble acid salts from the incoming waste stream of glycol feedstock to obtain a water/glycol phase substantially free of insoluble acid salts.

3. A system for removing impurities from an incoming waste stream of glycol feedstock according to claim 1, wherein the ester treatment device is further configured to inject a stoichiometric excess of the alkali solution into the incoming waste stream glycol feedstock sufficient to maintain a glycol feedstock comprising residual alkali solution and a pH of greater than 7.

4. A system for removing impurities from an incoming waste stream of glycol feedstock according to claim 3, wherein the alkali solution comprises at least one of sodium hydroxide and hydrogen peroxide.

5. A system for removing impurities from an incoming waste stream of glycol feedstock according to claim 1, further comprising a precipitation system disposed upstream of the ester treatment device, wherein the precipitation system is configured to:
receive the incoming waste stream of glycol feedstock;
determine a sulfate level within the incoming waste stream of glycol feedstock;
inject a sulfate precipitator into the incoming waste stream of glycol feedstock;
separate precipitated sulfate from the incoming waste stream of glycol feedstock to form the water/glycol phase; and
deliver the separated water/glycol phase to the ester treatment device.

6. A system for removing impurities from an incoming waste stream of glycol feedstock according to claim 5, wherein the precipitation system is further configured to maintain the separated water/glycol phase in an alkaline state.

7. A system for removing impurities from an incoming waste stream of glycol feedstock according to claim 5, wherein the sulfate precipitator comprises an alkali.

8. A system for removing impurities from an incoming waste stream of glycol feedstock according to claim 7, wherein the alkali comprises at least one of sodium hydroxide, potassium hydroxide, calcium hydroxide, magnesium hydroxide, and barium hydroxide.

9. A system for removing impurities from an incoming waste stream of glycol feedstock according to claim 1, further comprising a filter press disposed upstream of the ester treatment device, wherein the filter press is configured to:
remove an oligomer from a water/glycol phase of the incoming waste stream glycol feedstock; and
deliver the water/glycol phase having removed oligomer to the ester treatment device.

* * * * *